United States Patent
Kannengiesser et al.

(10) Patent No.: US 9,823,322 B2
(45) Date of Patent: Nov. 21, 2017

(54) METHOD AND APPARATUS FOR MAGNETIC RESONANCE DATA ACQUISITION USING A MULTIPOINT DIXON TECHNIQUE

(71) Applicant: Siemens Aktiengesellschaft, Munich (DE)

(72) Inventors: Stephan Kannengiesser, Wuppertal (DE); Marcel Dominik Nickel, Herzogenaurach (DE); Xiaodong Zhong, Lilburn, GA (US)

(73) Assignee: Siemens Healthcare GmbH, Erlangen (DE)

( * ) Notice: Subject to any disclaimer, the term of this patent is extended or adjusted under 35 U.S.C. 154(b) by 572 days.

(21) Appl. No.: 14/476,968

(22) Filed: Sep. 4, 2014

(65) Prior Publication Data
US 2015/0061672 A1    Mar. 5, 2015

(30) Foreign Application Priority Data

Sep. 4, 2013 (DE) .................. 10 2013 217 651

(51) Int. Cl.
| | |
|---|---|
| G01R 33/485 | (2006.01) |
| A61B 5/055 | (2006.01) |
| G01R 33/46 | (2006.01) |
| G01R 33/48 | (2006.01) |
| G01R 33/565 | (2006.01) |

(52) U.S. Cl.
CPC ............ *G01R 33/485* (2013.01); *A61B 5/055* (2013.01); *G01R 33/46* (2013.01); *G01R 33/4828* (2013.01); *G01R 33/56518* (2013.01); *G01R 33/56563* (2013.01)

(58) Field of Classification Search
CPC ...... A61B 5/055; G01R 33/485; G01R 33/46; G01R 33/4828; G01R 33/56518; G01R 33/56563
See application file for complete search history.

(56) References Cited

U.S. PATENT DOCUMENTS

| | | | |
|---|---|---|---|
| 5,627,469 | A | 5/1997 | Hong et al. |
| 6,091,243 | A | 7/2000 | Xiang et al. |

(Continued)

OTHER PUBLICATIONS

Berglund et al., "Three-Dimensional Water/Fat Separation and T*2 Estimation Based on Whole-Image Optimization—Application in Breathhold Liver Imaging at 1.5 T," Magnetic Resonance in Medicine, vol. 67, pp. 1684-1693 (2012).
Lu et al., "Multiresolution Field Map Estimation Using Golden Section Search for Water-Fat Separation," Magnetic Resonance in Medicine, vol. 60, pp. 236-244 (2008).
Yu et al., "Field Map Estimation with a Region Growing Scheme for Iterative 3-Point Water-Fat Decomposition," Magnetic Resonance in Medicine, vol. 54, pp. 1032-1039 (2005).

(Continued)

*Primary Examiner* — Gregory H Curran
(74) *Attorney, Agent, or Firm* — Schiff Hardin LLP

(57) ABSTRACT

In a method and magnetic resonance (MR) apparatus to acquire MR data from a subject, a predetermined spectral model of a multipoint Dixon technique is used that includes at least two spectral components with respective associated relaxation rates, a first phase due to field inhomogeneities; and a second phase due to eddy current effects. MR data are acquired using a bipolar multi-echo MR measurement sequence for multiple image points wherein, for each image point, the multi-echo MR measurement sequence alternately uses positive and negative readout gradient fields for the readout of MR signals of the MR data at at least three echo times. The at least two spectral components are determined based on the MR data.

25 Claims, 7 Drawing Sheets

(56) References Cited

U.S. PATENT DOCUMENTS

| 6,515,476 B1 | 2/2003 | Oshio et al. |
| 2002/0193680 A1 | 12/2002 | Feiweier |
| 2005/0030025 A1* | 2/2005 | Ma .................. A61B 5/055 |
| | | 324/309 |
| 2009/0072826 A1* | 3/2009 | Hargreaves ........ G01R 33/4828 |
| | | 324/309 |
| 2011/0140696 A1 | 6/2011 | Yu |
| 2015/0042334 A1 | 2/2015 | Kannengiesser et al. |
| 2015/0061667 A1 | 3/2015 | Nickel |

OTHER PUBLICATIONS

Golub et al., "The Differentiation of Pseudo-Inverses and Nonlinear Least Squares Problems Whose Variables Separate," SIAM Journal of Numer. Anal., vol. 10, No. 2 (1973), pp. 413-432.

Lu et al; Water-fat separation with bipolar multiecho sequences, Magn. Reson. Med, vol. 60, pp. 198-209, (2008).

Yu et al.: "Multiecho Water-Fat Separation and Simultaneous $R*2$ Estimation with Multifrequency Fat Spectrum Modeling"; Magn. Resonance in Medicine vol. 60 pp. 1122-1134; (2008).

Berglund et al.: "Three-Point Dixon Method Enables Whole-Body Water and Fat Imaging of Obese Subjects"; Magnetic Resonance in Medicine vol. 63, pp: 1659-1668; (2010).

Dongmei: A Novel Algorithm for Eddy Current Effect Elimination in Three Points Dixon Method, Proceedings of International Society for Magnetic Resonance in Medicine (CD-ROM), p. 3959; (2009).

* cited by examiner

METHOD AND APPARATUS FOR MAGNETIC RESONANCE DATA ACQUISITION USING A MULTIPOINT DIXON TECHNIQUE

BACKGROUND OF THE INVENTION

Field of the Invention

The invention concerns a method for magnetic resonance (MR) measurement (data acquisition) and a magnetic resonance system to implement such a method. In particular, the invention concerns techniques with which determination of first and second spectral components from MR data is possible.

Description of the Prior Art

In a magnetic resonance measurements data acquisition, it is possible to separate spectral components included in the MR data. The spectral components can represent different spin species, for example nuclear spins in a fat environment and in an aqueous environment. For this purpose, chemical shift imaging multi-echo magnetic resonance (MR) measurement sequences are often used within the context of Dixon techniques. Such techniques typically utilize the fact that the resonance frequency of nuclear spins depends on the molecular or, respectively, chemical environment. This effect is known as a chemical shift. Different spin species have different resonance frequencies, from which the measured spectrum of the MR data is composed. For example, the difference between two resonance frequencies of different spectral components can be expressed in ppm (parts per million).

The chemical shift between hydrogen nuclear spins in water as a first spectral component, and hydrogen nuclear spins in fatty acid chains as a second spectral component, is often used. In such a case, a water MR image and/or a fat MR image —i.e. individual MR images of the two spectral components—can be produced using MR data. This is of interest in a variety of applications, for example clinical and/or medical applications.

In order to be able to separate the spectral components from one another, MR signals are acquired at multiple echo times within the scope of the Dixon technique. The MR signals together form the MR data. The different spectral components have different phase positions at the different echo times. Using this effect, it is possible to determine the different spectral components separately.

For this purpose, a spectral model is generally used that links the measured or acquired MR data with different physically relevant variables. The different variables in particular include the different spectral components to be determined, as well as additional unknowns of the measurement system (depending on the precision, scope and complexity of the spectral model). It can then be possible to determine the spectral components considered in the spectral model for each image point of the MR data.

In principle, it can be worthwhile to use a relatively complex spectral model, for example such a spectral model which considers a large number of further unknowns in addition to the spectral components to be determined. It can then be possible to determine the spectral components particularly precisely. In this case, however, it can be necessary to acquire particularly many MR signals at different echo times, which can in turn extend a measurement duration and therefore can be disadvantageous. A trade-off situation thus often results between measurement duration and precision in the determination of the spectral components.

SUMMARY OF THE INVENTION

A need therefore exists for techniques that enable a relatively precise determination of spectral components but that require only a small number of MR signals at different echo times, so as to be acquired in a relatively short measurement duration.

This object is achieved according to the invention by a method for magnetic resonance measurement of at least two spectral components of an examination subject with a multipoint Dixon technique at at least three echo times. A predetermined spectral model of the multipoint Dixon technique includes at least the at least two spectral components with respective associated relaxation rates, a first phase due to field inhomogeneities, and a second phase due to eddy current effects. The method includes the acquisition of MR data with a bipolar multi-echo MR measurement sequence for multiple image points, wherein the multi-echo MR measurement sequence alternately uses positive and negative readout gradient fields for each image point for the readout of MR signals of the MR data at the at least three echo times. Furthermore, the method includes, based on the MR data: at least partial numerical determination of the at least two spectral components with the respective associated relaxation rates for each image point, as well as the first phase and the second phase.

For example, the field inhomogeneities can be spatial variations of a basic magnetic field of an associated MR system. It is typically desired that the basic magnetic field has no, or only a slight, spatial variation, so as to achieve homogeneous resonance conditions for nuclear spins that have no or only a slight dependency on their location in the basic magnetic field. However, the presence of field inhomogeneities often cannot be entirely precluded due to technical limitations. For example, eddy current effects can occur upon switching of gradient fields. The eddy current effects can have a dependency on the orientation of the gradient fields. For example, the eddy current effects assume qualitatively and/or quantitatively different values depending on the direction of a gradient field.

For example, the MR measurement can concern a fat component as a first spectral component and a water component as a second spectral component. For example, silicone could also be considered as an additional spectral component. These examples are not limiting.

The at least three echo times can typically be determined relative to a time period between an MR signal and a radiated radio-frequency (RF) excitation pulse. Within the scope of the MR measurement sequence, three or more echoes that correspond to the MR signals at the echo times can then be formed one after another.

The bipolar multi-echo MR measurement sequence can be a gradient echo sequence. In the bipolar gradient echo sequence, two successive gradient fields are typically used that are oriented in opposite directions, for example readout gradient fields along a direction designated as a readout direction. For example, the readout gradient fields that are oriented along a readout direction that is defined as positive can be designated as positive or even readout gradient fields. Readout gradient fields that are oriented along the negative readout direction (i.e. opposite the positive readout direction) can also be designated as negative or odd readout gradient fields. A dephasing with subsequent rephasing of a transverse magnetization can take place by the alternating even and odd readout gradient fields. For example, a shortened required total time to acquire the MR data (measurement duration) can be achieved, in particular in comparison to monopolar gradient echo sequences in which all readout gradient fields in which an MR signal is acquired are typically oriented in the same direction along the readout direction.

For example, it is possible for the readout gradient fields to be rectangular or trapezoidal in the time period and/or in the special domain. For example, it is furthermore possible for a chronological middle point of the readout gradient fields to be chronologically coincident with, or near to, a respective one of the at least one of the three echo times.

For example, in this regard it is possible for the at least three echo times to each have the same intervals at adjacent echo times, thus are equidistantly situated. In other words: the at least three echo times are situated in a fixed and uniform time spacing. For example, the at least three echo times can each be whole-number multiples of the first echo time.

For example, it is possible for the first phase and the second phase not to be determined separately for each image point, but rather to be determined the same for multiple adjacent image points. However, is also possible for the first phase and the second phase to be determined separately for each image point. The at least two spectral components can be determined individually for each image point.

In principle, a purely numerical determination may be limited compared to analytical techniques. For example, an optimization can be implemented within the scope of the purely numerical determination. The optimization can include, for example, iterative techniques, such as with regard to solutions of equations that are derived from the predetermined spectral model. In the present case, the numerical determination can also include one or more analytical calculation steps.

The at least partial numerical determination of the at least two spectral components with the respective associated relaxation rates for each image point and the first phase and second phase can be divided into multiple steps. For example, the first phase can initially be determined and the second phase can subsequently be determined, and following this the relaxation rates for each image point can be determined together with the at least two spectral components. Other sequences of the at least partially numerical determination are possible. For example, the second phase could be determined initially and subsequently the first phase; or, it would also be possible to initially determine the first and second phase simultaneously, such as within the scope of a common numerical optimization, and following this to determine the at least two spectral components with the respective associated relaxation rates for each image point. The at least partial numerical determination thus is not limited to the applied methods and sequences. Insofar as the at least partial numerical determination has multiple steps, each of the multiple steps can be composed of numerical techniques or analytical techniques, or mixtures of numerical and analytical techniques.

By the consideration of the second phase based on eddy current effects, the effect of a particularly precise determination of the at least two spectral components and of a particularly short measurement duration can be achieved, in particular in connection with the bipolar multi-echo MR measurement sequence. This is based on the insight that the eddy current effects typically show a dependency on the direction of the readout gradient fields. By the separate provision of the second phase based on eddy current effects in the spectral model, this dependency on the direction of the readout gradient fields can be used in the determination of the at least two spectral components, such that as a result the latter are not adulterated (or are only slightly adulterated) due to this dependency. It is possible to use the bipolar gradient echo MR measurement sequence, which reduces the measurement duration, particularly in comparison to a case in which a monopolar gradient echo MR measurement sequence is used.

For example, the method can furthermore include the provision of an MR image for each of the at least two spectral components of the examination subject. In a simple embodiment, for example, a fat MR image can be provided for a fat component of the examination subject and a water MR image can be provided for a water component of the examination subject. Subsequent clinical diagnostics can be made based on the provided MR images.

As a further effect, the provided MR images have a relatively low signal noise, or depict the respective spectral components with a particularly high precision. A reliable quantification (of the fat content or of the water content, for example) thus can be made.

For example, the predetermined spectral model can include a positive prefactor of the second phase for those MR signals of the MR data that are read out given positive readout gradient fields. For example, the predetermined spectral model can include a negative prefactor of the second phase for those MR signals of the MR data that are read out given negative readout gradient fields.

The positive and negative readout gradient fields can have equal but oppositely oriented amplitudes. A particularly simple, at least partially numerical determination of the at least two spectral components etc. can take place by the provision of the positive prefactor for positive readout gradient fields or of the negative prefactor for negative readout gradient fields. This is based on the fact that the influence of the eddy current effects on the phase of the nuclear spins is qualitatively the same for the positive and negative readout gradient fields, but quantitatively differs by a positive or negative prefactor.

Furthermore, the method can include determination of (for example) a computational grid with low resolution in comparison to the MR data, wherein each grid point of the computational grid includes a predetermined number of adjacent image points of the MR data. The at least partial numerical determination of the first phase and second phase can be based on at least one equation that takes into account that the first phase and/or the second phase is constant within a grid point of the computational grid.

For example, the determination of the computational grid can furthermore include the establishment of the predetermined number of adjacent image points of the MR data that are represented by a grid point, depending on a user input and/or a machine parameter of a magnetic resonance system.

The resolution of the MR data can be determined by a variable of an image point of the MR data, for example as a number of image points per area. The resolution of the computational grid can be determined accordingly, such as by a variable of a grid point, for example.

In other words, a grid point of the computational grid can designate that region within which the first phase and/or the second phase are each assumed to be constant, i.e. have a fixed value. The scale of a grid point of the computational grid can correlate with that length scale at which it is assumed that the first phase and/or the second phase exhibit no significant change. Stated more generally, it can be assumed that the first phase and/or the second phase is/are constant in subsets thereof. This forms the basis of the realization that the field inhomogeneities and the eddy current effects typically vary less strongly in position (exhibit a smaller spatial dependency) than, for example, the at least two spectral components.

When finding a solution for the first phase and/or the second phase it can be taken into account that these are constant in subsets thereof. This is different compared to various known implementations. In various known implementations, the low spatial dependency of the field inhomogeneities and the eddy current effects are typically taken into account only after identifying the first phase and the second phase: a numerical optimization that is used in this regard typically delivers a number of result candidates for the first phase and the second phase, for example for every image point of the MR data. From this number of result candidates, a value can then be selected (assuming the lower spatial dependency of the field inhomogeneities and the eddy current effects) as a solution of the first phase and the second phase, for example within the scope of a region growing technique. In other words, the numerical optimization is implemented with a relatively high spatial resolution, in which the lower spatial dependency of the field inhomogeneities and the eddy current effects is not taken into account, or is only taken into account to a limited extent, and only thereafter are the lower spatial dependency of the field inhomogeneities and the eddy current effects taken into account in discovery of the actual physically relevant solution from the plurality of result candidates.

For example, a grid point can be quadratic or rectangular, i.e. can include a different number of image points of the MR data along different spatial directions. More complex influences of varying unknowns that have spatial dependencies of different strengths for different spatial directions thus can be taken into account. Solely as an example, a grid point of the computational grid can include 2×2 or 2×4 or 6×6 or 20×20 or 100×50 image points of the MR data. It would also be possible for the size of a grid point of the computational grid to be different at various locations. For instance, more complex spatial dependencies of the field inhomogeneities and/or of the eddy current effects can therefore be considered.

As described above, at a relatively early point in time in the at least partially numerical determination of the first phase and the second phase, it can already be considered that the first phase and/or the second phase have a relatively low spatial dependency, for example to be constant within a grid point of the computational grid. For example, at the point in time of the implementation of a numerical optimization it can thus already be taken into account that the first phase and/or the second phase have a lower spatial dependency than the MR data themselves. The effect of a relatively efficient and less computationally intensive numerical optimization thus can be achieved, particularly in comparison to reference implementations in which only after a numerical optimization (for example upon discovering result candidates, for instance within the scope of a region growing technique) is it considered that portions of the first phase and/or the second phase are constant.

The effect of a particularly precise determination of the first spectral component and of the second spectral component can thereby also be achieved. This is the result of a higher signal-to-noise ratio of the phase images being achieved by the assumption that the first phase and/or the second phase is constant in subsets within the grid point, and as a result a higher signal-to-noise ratio of the spectral components subsequently calculated based on these is also achieved.

The at least partial numerical determination can include the following steps. A first numerical optimization is implemented that determines the first phase. The acquired are purged of MR data of influences of the first phase depending on the determined first phase. A second numerical optimization is then implemented that determines the second phase. The acquired MR data are purged of influences of the second phase depending on the determined second phase.

In general, the first and second numerical optimization can be implemented based on any optimization technique known to those skilled in the art. For example, the optimization can be a chi-square optimization or an Lp-norm optimization. For example, the optimization problems can be solved by the Marquardt-Levenberg method.

For example, the purging of the acquired MR data means influences of the first phase or of the second phase are reduced, for example by computationally eliminating the influences, or by correcting the acquired MR data. For example, given knowledge of the first phase and/or of the second phase, it is possible to correct the acquired MR data so that the field inhomogeneities and/or the eddy current effects have no or only a slight influence on the MR data after the purging.

For example, the first numerical optimization and the corresponding purging of the acquired MR data of influences of the first phase can be implemented before the second numerical optimization. It is also possible for the second numerical optimization and the corresponding purging of the acquired MR data of influences of the second phase to be implemented initially, and the first numerical optimization and the corresponding cleaning to be subsequently implemented.

In other words: the at least partial numerical determination can thus be implemented in stages or, respectively, parts, but with fundamentally variable order (sequencing). The effect of an increased precision thus can be achieved in the determination of the first and second spectral component. At the same time, the required computing capacities can be relatively small.

For example, it is possible for the first numerical optimization to be implemented based on a first equation that takes into account that the first phase and/or the second phase is constant within a grid point of the computational grid. Alternatively or additionally, it is possible for the second numerical optimization to be implemented based on a second equation that takes into account that the first phase and/or the second phase is constant within a grid point of the computational grid. A relatively less computationally intensive implementation of the first and/or second numerical optimization can be achieved.

The implementation of the first numerical optimization can provide multiple result candidates for an image point. The first optimization can furthermore include the implementation of a region growing technique for the multiple image points of the MR data in order to select a value for each image point from the multiple result candidates as a result. Alternatively or additionally, the implementation of the second numerical optimization can provide multiple result candidates for an image point, wherein the second optimization furthermore includes the implementation of a region growing technique for the multiple image points of the MR data in order to select a value for each image point from the multiple result candidates as a result.

In general, the region growing technique can take into account results of the numerical optimization for adjacent image points of the MR data, i.e. select the first phase and/or the second phase for adjacent image points based on an initial image point for respective adjacent image points. Appropriate techniques are known to those skilled in the art, for example from H. Yu et al. "Field map estimation with a region growing scheme for iterative 3-point water-fat-decomposition" in Mag. Reson. Met. 54 (2005), 1032-1039. Therefore, additional details need not be explained herein with regard to the region growing technique.

By the implementation of the region growing technique, a reliable and precise discovery of the actual physically relevant solution from multiple result candidates can be ensured. The precision can be further increased in the determination of the at least two spectral components.

For example, an equation on which the first numerical optimization is based and/or an equation on which the second numerical optimization is based has no explicit dependency on at least one of the at least two spectral components. For example, the equation can have no dependency on each of the at least two spectral components.

It is therefore possible to inherently take into account the at least two spectral components in the implementation of the first numerical optimization and/or in the implementation of the second numerical optimization. It is thereby achieved that the precision of the determination of the first and/or second spectral component is not, or is only slightly, decreased within the scope of the implementation of the first and/or second numerical optimization. In particular, it can be worthwhile to use an approximation or other numerical assumptions for the at least two spectral components within the scope of the implementation of the first and/or second numerical optimization.

For example, the equation on which the first numerical optimization is based can be described by a variable projection of complex-valued weightings of the two spectral components. For example, the equation on which the second numerical optimization is based can be described by a variable projection of real-value weightings of the two spectral components.

However, it is also be possible, for example, that both the equation on which the numerical optimization is based and the equation on which the second numerical optimization is based are based on a variable projection of real-value or complex-valued weightings.

In general, techniques of variable projection are known to those skilled in the art, for example from the article by G. H. Golub and V. Pereyra "The differentiation of pseudoinverses and nonlinear least squares problems whose variables separate" in SIAM J. Numer. Anal. 10 (1973), 413-432. Therefore, additional details with regard to the variable projection need not be provided herein.

For example, the complex-valued weightings of the at least two spectral components can take into account (for example) an amplitude and a phase within the scope of the real part and the imaginary part. It is thus already possible, via the use of the complex-valued weightings, to use a relative phase position between the at least two spectral components.

It is also possible for the equation on which the second numerical optimization is based to furthermore include a phase at the first echo time. This can be worthwhile when the equation on which the second numerical optimization is based takes into account real-value weightings of the at least two spectral components. A relative phase position between the at least two spectral components over the phase at the first echo time can then be considered.

By considering a relative phase position, for example, diverse excitation effects within the scope of the radiation of the RF excitation pulse can be taken into account.

For example, an equation on which the first numerical optimization is based can have no explicit dependency on the second phase. For example, an equation on which the second numerical optimization is based can have no explicit dependency and no implicit dependency on the first phase.

For example, by computational elimination of the second phase in the equation on which the first numerical optimization is based it can be achieved that the equation has no explicit dependency on the second phase. Also as an example, by purging the acquired MR data of influences of the first phase depending on the determined first phase it can be achieved that the equation on which the second numerical optimization is based has neither an explicit nor an implicit dependency on the first phase, since its influence has been computationally eliminated.

For example, if the second numerical optimization is implemented before the first numerical optimization, it is then possible for the equation on which the second numerical optimization is based to have no explicit dependency on the first phase, and for the equation on which the first numerical optimization is based to have no explicit dependency and no implicit dependency on the second phase.

The computational elimination and/or the purging of the acquired MR data of respectively the first phase and/or the second phase, allows the implementation of the first and second numerical optimization to inherently take their influences into account. The precision in the determination of the at least two spectral components thus can be further increased.

It is also possible for an equation on which the first numerical optimization is based to assume a relaxation rate for the at least two spectral components that is equal to zero. Alternatively or additionally, it is possible for an equation on which the second numerical optimization is based to assume a relaxation rate for the at least two spectral components that is equal to zero.

In other words, in advance of the determination of the at least two spectral components with the respective associated relaxation rates for each image point, the relaxation rate can be assumed as zero as a simplification. In a subsequent step in which the relaxation rates and/or the at least two spectral components are themselves determined, this assumption can be abandoned. At the same time, a precise determination of the at least two spectral components and of the relaxation rates can take place while the required computing capacities can also be limited, in particular within the scope of the implementation of the numerical optimizations to determine the first phase and the second phase.

In the preceding, techniques have been described primarily in relation to the determination of the first phase and/or the second phase. In the following, techniques are explained that primarily concern the determination of the at least two spectral components as well as the associated relaxation rates.

It is possible for the determination of the at least two spectral components with the respective associated relaxation rates to include the following steps. A numerical optimization is implemented that determines the relaxation rates of the at least two spectral components, and analytical calculation of the at least two spectral components is implemented depending on the determined relaxation rates.

It is possible for the implementation of the numerical optimization to determine the relaxation rates of the at least two spectral components to provide multiple result candidates for an image point, with one of the multiple result candidates being selected based on a derivation of an equation on which this numerical optimization is based.

Alternatively or additionally, it is possible to apply a region growing technique to select one of the multiple result candidates.

An equation on which the numerical optimization to determine the relaxation rates is based can have no dependency on the first phase and/or on the second phase. The dependency on the first phase and/or second phase can be eliminated by preceding numerical determination of the first phase and/or of the second phase and purging of the influence of the first phase and/or the second phase on the MR data.

For example, the implementation of the numerical optimization that determines the relaxation rates of the at least two spectral components can be based on an equation that has no explicit dependency and no implicit dependency on the first phase and/or on the second phase. For example, an explicit dependency and an implicit dependency on the first phase and/or on the second phase can be eliminated by cleaning the acquired MR data of influences of the first phase and/or of the second phase. By computational elimination of the first phase and/or of the second phase from the equation on which the numerical optimization to determine the relaxation rates of the at least two spectral components is based, it could accordingly be achieved that this has no implicit dependency on the first phase and/or the second phase. A particularly precise determination of the at least two spectral components can thereby be achieved since the influences of the first phase and/or the second phase do not need to be approximated within the scope of the implementation of the numerical optimization to determine the relaxation rates.

An equation on which the numerical optimization is based to determine the relaxation rates can have no explicit dependency on the at least two spectral components. It is possible that the equation on which the numerical optimization to determine the relaxation rates is based is described by a variable projection of weightings of the two spectral components.

The present invention also concerns an MR system that is set up for MR measurement of at least two spectral components of an examination subject by means of a multipoint Dixon technique at at least three echo times. The MR system has an acquisition unit and a computer. The acquisition unit is designed in order to acquire MR data by implementing a bipolar multi-echo MR measurement sequence for multiple image points. For each image point, the multi-echo MR measurement sequence alternately uses positive and negative readout gradient fields for the readout of MR signals of the MR data at the at least three echo times. The computer is designed to at least partially numerically determine— based on the MR data—the at least two spectral components with the respective associated relaxation rates for each image point, as well as the first phase and the second phase.

The MR system according to the invention is designed to implement the method according to the present invention.

The advantages of the MR system according to the invention are analogous to the advantages described above with regard to the method according to the invention.

DESCRIPTION OF THE PREFERRED EMBODIMENTS

Figure 1:
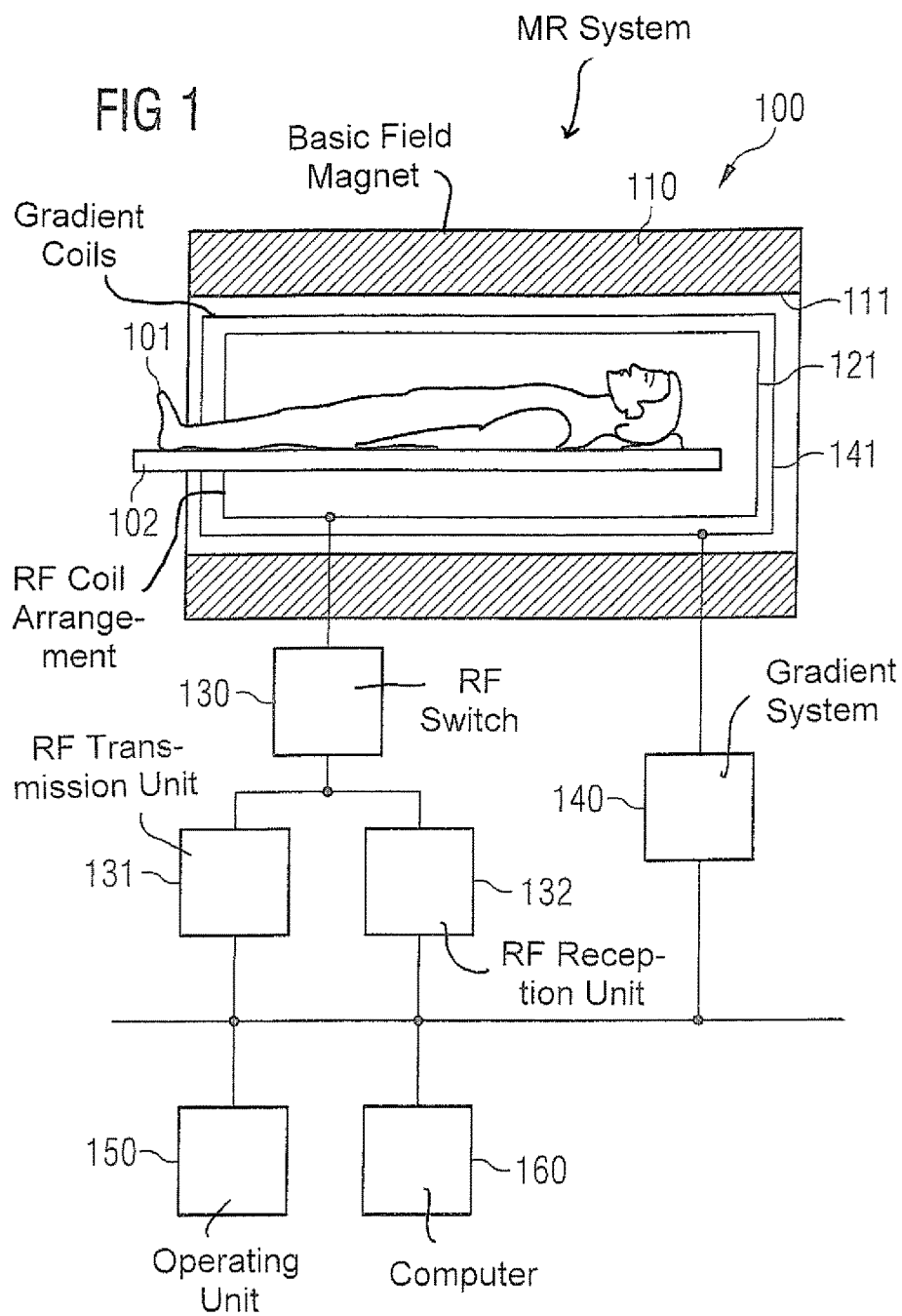
FIG. 1 is a schematic illustration of an MR system.

In the following, the present invention is explained in detail using preferred embodiments with reference to the drawings. In the figures, identical reference characters designate identical or similar elements. The subsequent description of embodiments with reference to the figures should not be construed as limiting. The figures are purely illustrative.

The figures are schematic representations of different embodiments of the invention. Elements presented in the figures are not necessarily shown true to scale. Rather, the different elements presented in the figures are rendered such that their function and general purpose are comprehensible to those skilled in the art. Connections and couplings between functional units and elements that are depicted in the figures can be implemented as indirect connections or couplings. A connection or coupling can be implemented via wires or wirelessly. Functional units can be implemented as hardware, software or a combination of hardware and software.

In the following, techniques are presented by means of which at least a first spectral component and a second spectral component are determined from MR data. For example, the first spectral component can indicate a fat content (shortened to fat in the following) and the second spectral component can indicate a water content (shortened to water in the following). In general, however, any spin species can be considered, thus also silicone, for instance.

The MR data are acquired with a multipoint Dixon technique, thus the MR data are acquired from at least three MR signals respectively at different echo times. A spectral model is also used that, in addition to the fat component and water component, also takes into account a first phase due to field inhomogeneities and a second phase due to eddy current effects. Weightings of the fat component and of the water component that are considered in the spectral model can typically be assumed to be real values, but it is also possible to assume the weightings to be complex-valued.

The signal $D_e(x)$ in the image point x can be modeled via the following spectral model:

$$D_e(x) = \left(d_e e^{-R^*_{2,water}(x) T_{E,e}} W(x) + c_e e^{-R^*_{2,fat}(x) T_{E,e}} F(X)\right) \quad (1)$$
$$e^{i\Omega(x) T_{E,e} + i\phi(x) + i a_e \phi_{EC}(x)},$$

wherein e designates the MR signals at various echo time $T_{E,e}$, $W(x)$ corresponds to the weighting of the water component, $F(x)$ corresponds to the weighting of the fat component, and $R^*_{2,water}(x)$ and $R^*_{2,fat}(x)$ are relaxation constants for the water component and fat component. Furthermore, $\Omega(x)$ designates the first phase, $\phi(x)$ designates a phase at the first echo time, and $\phi_{EC}(x)$ designates the second phase. The prefactor $\alpha_e$ for the second phase is either +1 or −1, depending on an orientation of the readout gradient field. In the following, a direction of the readout gradient field is designated as even if $\alpha_e=+1$ and the opposite direction is designated as odd if $\alpha_e=-1$. $d_e$ and $c_e$ also designate predetermined phase factors for each MR signal that respectively designate the phase evolution of the water component and of the fat component. For water, $d_e=1$ is assumed in the following, while $c_e$ can be calculated. It is possible that $d_e$ and $c_e$ are predetermined.

In general, the weightings W and F are chosen to be complex-valued, wherein in such a case the phase $\phi(x)$ at the first echo time is equal to zero. However, it is also possible that W and F are assumed to have real values, wherein in such a case the phase $\phi(x)$ at the first echo time can be designated as the phase that is extrapolated directly after the excitation.

The spectral model discussed in the preceding can also be represented as $$D = \phi A v, \quad (2)$$

wherein $$v(x) = \begin{pmatrix} W(x) \\ F(x) \end{pmatrix}, D(x) = \begin{pmatrix} D_1(x) \\ \vdots \\ D_{N_e}(X) \end{pmatrix},$$

$$A = \begin{pmatrix} d_1 e^{-R_{2,water}^*(x)T_{E,1}} & c_1 e^{-R_{2,fat}^*(x)T_{E,1}} \\ \vdots & \vdots \\ d_{N_e} e^{-R_{2,water}^*(x)T_{E,1}} & c_{N_e} e^{-R_{2,fat}^*(x)T_{E,1}} \end{pmatrix},$$

$$\phi(x) = \begin{pmatrix} \exp(i\Omega(x)T_{E,1} + i\alpha_1\phi_{EC}(x) + i\phi(x)) & & \\ & \ddots & \\ & & \exp(i\Omega(x)T_{N_e} + i\alpha_{N_e}\phi_{EC}(x) + i\phi(x)) \end{pmatrix}, \quad (3)$$

and $N_e$ designates the number of echoes.

In a simple embodiment, the following equation can be optimized within the scope of a chi-square optimization:

$$x^2 = \|\phi A v - D\|^2, \quad (4)$$

For example, this can take place separately for each image point. In such a case, however, ambiguities can occur in the solution. The underlying problem is that the problem described by Equation (4) has different local minima in $\Omega$ and $\phi_{EC}$. In particular, the problem described by Equation (4) is periodic if the echo times are equidistant. In such a case, the global minimum may not coincide with the actual physical condition due to the noise and imperfections of the considered spectral model.

Therefore, it is assumed that the field inhomogeneities have a relatively low spatial dependency, meaning that the first phase $\Omega(x)$ varies relatively less strongly in location. This information can be used to determine a solution to Equation (4). A corresponding assumption can be made for the eddy current effects. In the present approach, for example, via the assumption of the first phase and/or second phase these can be considered to be constant in parts.

In other words: the predetermined spectral model according to Equations (1)-(3) includes at the at least two spectral components F, W with respective associated relaxation rates, a first phase $\Omega$ due to field inhomogeneities and a second phase $\phi_{EC}$ due to eddy current effects.

As noted, a spectral model corresponding to Equation (1) can also be directly set up for other species than fat and water, but for simplicity only water and fat are referred to for the purpose of better illustration.

In the following, techniques are now explained which enable a determination of the first and second spectral components W(x), F(x) on the basis of the spectral model, i.e. on the basis of Equations 1-3. However, the fundamentals of the MR system that can be used for the MR measurement are initially explained with reference to FIG. 1.

In FIG. 1, an MR system 100 is shown which is designed to implement techniques, methods and steps according to the invention. The MR system 100 has a magnet 110 that defines a tube 111. The magnet 110 can generate a basic magnetic field parallel to its longitudinal axis. The basic magnetic field can exhibit inhomogeneities, thus local deviations from a desired value. An examination subject (here an examined person 101) can be slid on a bed table 102 into the magnet 110. Furthermore, the MR system 100 has a gradient system 140 to generate gradient fields that are used for MR imaging and for spatial coding of acquired raw data. The gradient system 140 typically has at least three gradient coils 141 that are separately controllable and positioned with good definition relative to one another. The gradient coils 141 enable gradient fields to be applied and switched along defined spatial directions (gradient axes). By switching the gradient fields, eddy current effects can be caused which produce local magnetic fields. The gradient fields can be used for slice selection, for frequency coding (in the readout direction) and for phase coding, for example. A spatial coding of the raw data is thereby achieved. The spatial directions that are respectively parallel to slice selection gradient fields, phase coding gradient fields and readout gradient fields do not necessarily need to be coincident with the machine coordinate system. Rather, they can be defined in relation to a k-space trajectory (for example) which can in turn be established on the basis of specific requirements of the respective MR measurement sequence and/or can be established based on anatomical properties of the examined person 101.

To excite the nuclear spins (i.e., to deflect them from the polarization or alignment from the magnetization in the longitudinal direction that result in the basic magnetic field) an RF coil arrangement 121 is provided that radiates an amplitude-modulated RF excitation pulse in the examined person 101. A transverse magnetization of the nuclear spins is thereby produced. To generate such RF excitation pulses, an RF transmission unit 131 is connected via an RF switch 130 with the RF coil arrangement 121. The RF transmission unit 131 can have an RF generator and an RF amplitude modulation unit. The RF excitation pulses deflect ("flip") the nuclear spins out of the steady stage to produce the transversal magnetization in 1D (slice-selectively) or 2D/3D (spatially selectively or globally).

Furthermore, an RF acquisition unit 132 is coupled via the RF switch 130 with the RF coil arrangement 121. With the RF acquisition unit 132, MR signals of the relaxing transverse magnetization (for example due to inductive injection into the RF coil arrangement 121) can be acquired as MR data.

In general, it is possible to use separate RF coil arrangements 121 for the radiation of the RF excitation pulses by means of the RF transmission unit 131 and for the acquisition of the MR data by means of the RF acquisition unit 132. For example, a volume coil 121 can be used for the radiation of RF pulses and a surface coil (not drawn), which may be an array of RF coils, can be used for the acquisition of raw data. For example, the surface coil can include 32 individual RF coils for the acquisition of the raw data, and therefore can be particularly suitable for partially parallel imaging (PPA, partially parallel acquisition). Appropriate techniques are known to those skilled in the art, and thus need not be explained in detail herein.

The MR system 100 furthermore has an operating unit 150 that, for example, can include a monitor, a keyboard, a mouse etc. User entries can be detected and displayed as an output to the user by the operating unit 150. For example, via the operating unit 150, individual operating modes or operating parameters of the MR system can be set by the user and/or automatically and/or via remote control.

Furthermore, the MR system 100 has a computer 160. For example, the computer 160 is configured to implement diverse computation operations within the scope of the determination of the fat component and the water component. For example, the computer 160 can be configured to implement a numerical optimization and/or analytical computation steps; and/or to eliminate influences of the first and/or second phase from the MR data; and/or to process MR data with a Fourier transformation.

Figure 2:
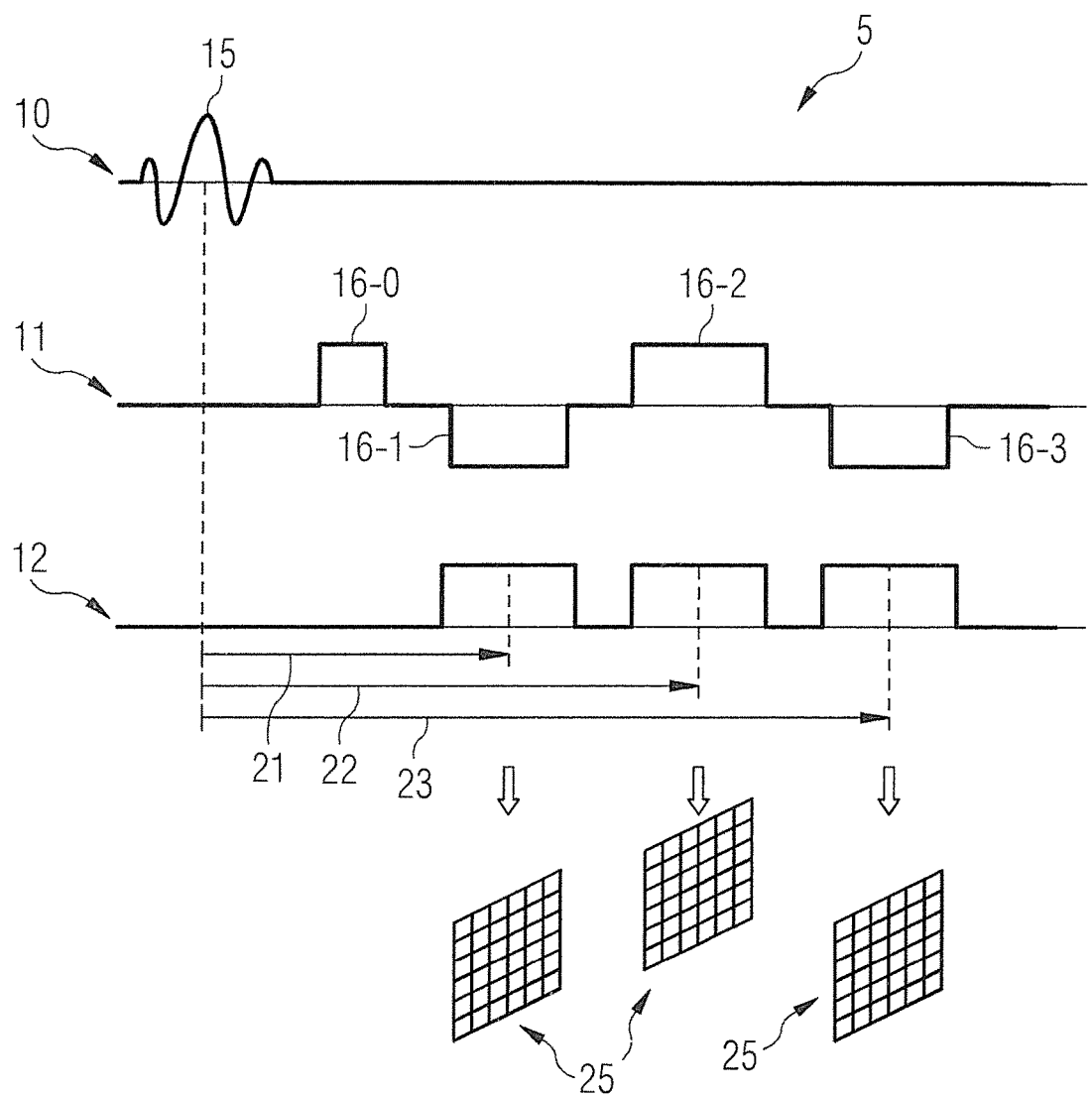
FIG. 2 shows a gradient echo MR measurement sequence in which three MR signals are acquired in a bipolar manner as MR data, respectively at a first echo time, at a second echo time and at a third echo time.

In FIG. 2, a three-point Dixon gradient echo MR measurement sequence 5 is shown. A radio-frequency 10, a gradient field component 11 and a readout channel 12 are shown. An RF excitation pulse 15 is initially radiated. Readout gradient fields 16 are subsequently switched (activated) that form three gradient echoes at the first echo time 21 and the second echo time 22 and the third echo time 23. The MR data 25—namely one MR signal at each echo time 21, 22, 23—are received by the analog/digital converter, graphically indicated by the measurement blocks on the readout channel 12. The echo times 21, 22, 23 are defined in relation to appoint in time known as the isodelay point in time of the RF excitation pulse 15 which, for example, lies approximately in the middle of the RF excitation pulse with a SINC amplitude envelope. Other definitions of the echo times 21, 22, 23 are possible and do not need to be discussed in detail in this context.

FIG. 2 is a simplified presentation since at least one slice selection gradient field and one phase coding gradient field (which are typically required for complete spatial coding of an image point of the MR data 25) are not shown. However, the MR data 25 are obtained with resolution for different image points (illustrated by the grid in FIG. 2), such that the additional gradient fields are also typically used for spatial coding.

Within the scope of a multipoint Dixon MR measurement sequence, MR signals can also be acquired at more than three echo times 21, 22, 23. For example, this can take place by continuing the application of the alternating readout gradient fields 16-1, 16-2, 16-3.

Figure 3:
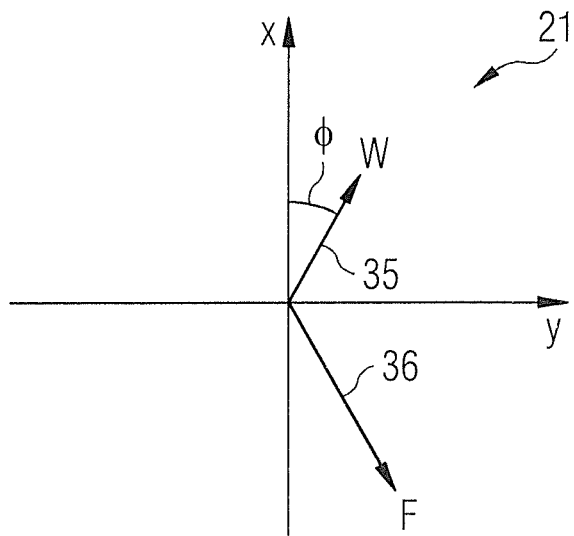
FIG. 3 illustrates a phase at the first echo time.

The RF excitation pulse 15 deflects the magnetization out of its steady state along the longitudinal direction, so that the aforementioned transverse component is produced. The transverse component is typically in the x-y plane (see FIGS. 3 and 4). In FIG. 3, the phase position of the water component 35 and of the fat component 36 at the first echo time 21 is shown. In particular, in FIG. 3 a situation is shown in which the MR measurement sequence 5 is adjusted to the water component 35. As can be seen from FIG. 3, the water component 35 has a phase $\phi$ relative to a zero degree position (defined as a reference) along the x-axis. Due to the frequency shift between the water component 35 and the fat component 36, the fat component 36 has a different phase position than the water component 35.

Figure 4:
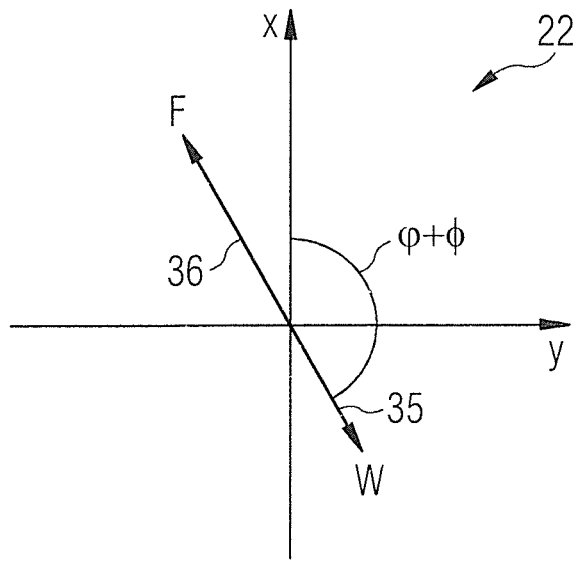
FIG. 4 illustrates a phase at the second echo time.

In FIG. 4, the phase position of the water component 35 and of the fat component 36 at the second echo time 22 is shown. Now the water component 35 has a phase shift relative to the zero degree position (defined as a reference phase) along the x-axis of $\phi+\varphi$. The phase evolution $\varphi$ thus designates an additionally acquired phase between the first and second echo times 21, 22 that is due to the field inhomogeneities and eddy current effects. The phase evolution $\varphi$ is thus composed of the first phase $\Omega(x)$ and the second phase $\phi_{EC}$.

Figure 5:
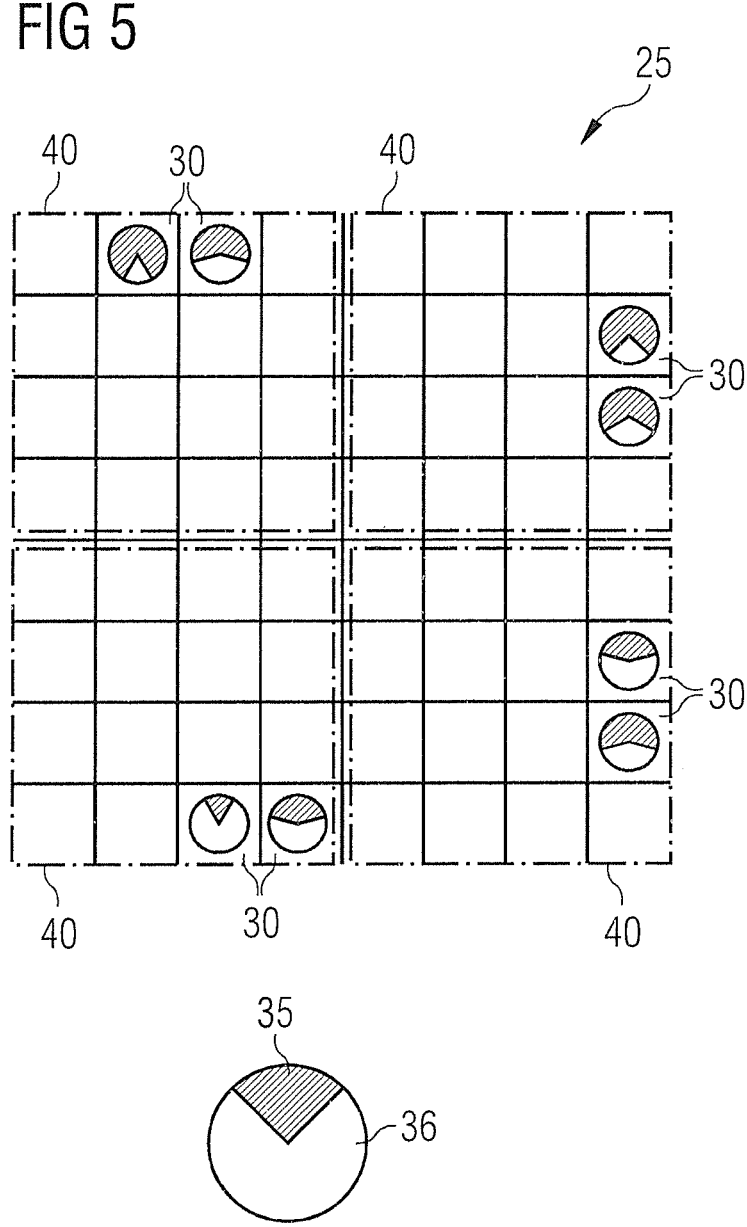
FIG. 5 schematically shows image points of the MR data, grid points of a computational grid, and a first and second spectral component for the different image points.

As is explained in the preceding with regard to Equations 1-4, the spectral model can be used to determine the water component 35 and the fat component 36, respectively for each image point 30 of the MR data 25 (see FIG. 5). The determination can take place at least partially in a numerical manner. For example, a numerical optimization can be implemented within the scope of the numerical sub-steps of the determination (see Equation (4)). It is now possible that the equation on the basis of which a numerical optimization is implemented—for example to determine the first phase $\Omega(x)$ and/or the second phase $\phi_{EC}(x)$—has no explicit dependency on the water component 35 and the fat component 36.

Alternatively or additionally, the first phase $\Omega(x)$ and/or the second phase $\phi_{EC}(x)$ can be assumed to be constant within a defined region. This is shown in FIG. 5. In FIG. 5, grid points 40 of a computation grid are represented with dashed lines. The image points 30 of the MR data 25 are also represented with solid lines in FIG. 5. As can be seen from FIG. 5, the computation grid is defined such that it is of low resolution in comparison to the MR data 25, meaning that a grid point 40 is larger than an image point 30. Each grid point 40 includes a predetermined number of adjacent image points 30 of the MR data 25; in the case of FIG. 5, 16 image points 30 are respectively included given quadratic grid points 40. For example, within the scope of the determination of the computation grid, the number of adjacent image points 30 of the MR data 25 that are included by a grid point 40 are established depending on a user input and/or depending on a machine parameter of the MR system 100.

The water component 35 and the fat component 36 in FIG. 5 are illustratively depicted for only a few image points 30 of the MR data 25. In general, however, it is possible to determine the water component 35 and the fat component 36 for all image points 30 of the MR data 25, for example to determine them individually.

In the following, techniques are presented in which it is assumed, within the scope of a numerical optimization, that the first phase $\Omega(x)$ and/or the second phase $\phi_{EC}(x)$ are respectively constant within a grid point 40 of the computation grid. The first phase $\Omega(x)$ and/or the second phase $\phi_{EC}(x)$ can thus also be designated as constant in parts subparts). It is therefore possible to particularly simply determine the water component 35 and the fat component 36.

In the example of FIG. 5, the grid points 40 for the first phase $\Omega(x)$ and the second phase $\phi_{EC}(x)$ have the same values. In general, however, it is possible that the first phase $\Omega(x)$ and the second phase $\phi_{EC}(x)$ are assumed to be constant in parts within different regions. In other words: different computation grids with different grid points 40 for the first phase $\Omega(x)$ and the second phase $\phi_{EC}(x)$ can be used.

Starting from Equation (4), the formulation can then be made:

$$x_u^2 = \sum_{x \in} \|\phi A v(x) - D(x)\|^2, \quad (5)$$

wherein $U=N_x \times N_y \times N_z$ designates the computation grid, and U designates a grid point 40.

For example, it is possible to determine the first phase $\Omega(x)$ within the scope of a first numerical optimization; the acquired MR data are subsequently purged of influences of the (now determined) first phase $\Omega(x)$. The second phase $\phi_{EC}(x)$ can subsequently be determined within the scope of a second numerical optimization, and the acquired MR data can be purged of influences of the (now determined) second phase.

For example, in this regard it is possible for the equation on which the first numerical optimization is based to have no explicit dependency on the water component 35 and the fat component 36. It is accordingly possible for the equation on which the second numerical optimization is based has no explicit dependency on the water component 35 and the fat component 36. For example, this explicit dependency can be eliminated a variable projection in relation to the water component 35 and the fat component 36, based on the spectral model or, respectively, Equation (5). Such a variable projection is in principle possible independent of whether the weightings W, F of the water component 35 and the fat component 36 are assumed to be complex-valued or real values. For example, it is possible for the equation on which the first numerical optimization is based to be described by a variable projection of complex-valued weightings W, F of the water component 35 and the fat component 36. This variable projection under the assumption of complex-valued weightings W, F is explained in the following.

Equation (5) is sesquilinear in v(x). The parameters included in v(x) can be determined as a function of $\phi$ and A. The minimum of Equation (5) results at $$v(x) = (A^T A)^{-1} A^T \phi^T D(x) \quad (6)$$

Insertion of Equation (6) into Equation (5) yields:

$$x_{local}^2 = \sum_{x \in u} D(x)^T D(x) - \sum_{x \in u} D(x)^T \phi P P^T \phi^T D(x), \quad (7)$$

wherein $$PP^T = A(A^T A)^{-1} A^T \quad (8)$$

The matrix defined by Equation (8) is a 2nd order positive Hermitian matrix with eigenvalues equal to 1. This means that this matrix according to Equation (8) is a projector and is the reason why the applied techniques are called "variable projection" techniques herein. The matrix P is not unique; the two columns merely need to form an orthonormal basis of the image of A. A possible selection is P=U, wherein U is part of the singular value decomposition $A = U\Sigma V^T$. In the following, it applies that: $P=(p_1, p_2)$.

It is also possible that the equation on which the first numerical optimization is based has no explicit dependency on the second phase $\phi_{EC}(x)$. This is possible because the optimization of the second phase $\phi_{EC}$ can also be addressed analytically. For this purpose, the MR signals are divided up into even MR signals (for which it applies that $\alpha_E=1$) and odd signals (for which it applies that $\alpha_E=-1$). With this differentiation it is obtained:

$$x_{local}^2 = \sum_{x \in u} D(x)^T D(x) - \sum_{x \in u, e \in even, e' \in even} \Psi_e D_e(x)^T (PP^T)_{ee'} D_{e'}(x) \Psi_{e'}^* - \quad (9)$$
$$\sum_{x \in u, e \in odd, e' \in odd} \Psi_e D_e(x)^T (PP^T)_{ee'} D_{e'}(x) \Psi_{e'}^* -$$
$$2\text{Re}\left(e^{2i\phi EC} \sum_{x \in u, e \in odd, e' \in even} \Psi_e D_e(x)^T (PP^T)_{ee'} D_{e'}(x) \Psi_{e'}^*\right),$$

where $\Psi^e = e^{i\Omega T e}$ has been inserted. This notation of Equation (9) can be simplified. For this, the MR signals are rearranged such that the continuous index e initially includes even MR signals and then includes odd MR signals. In this regard it can be written $$\Psi = \begin{pmatrix} \Psi_E \\ \Psi_O \end{pmatrix}, M = \begin{pmatrix} E & C \\ C^T & O \end{pmatrix}, \quad (10)$$

wherein E designates even MR signals and O designates odd MR signals. The matrix M is Hermitian and can respectively be calculated once for each grid point 40 of the computation grid. In this notation, $$x_{local}^2 = \sum_{x \in u} D(x)^T D(x) - \Psi_E^T E \Psi_E - \Psi_O^T O \Psi_O - 2\text{Re}(e^{2i\phi EC} \Psi_E^T O \Psi_O) \quad (11)$$

is obtained.

Equation (11) is minimized for $e^{2i\phi Ec} = (\Psi_E^T O \Psi_O)^* / |\Psi_E^T O \Psi_O|$. Therefore, the following equation can be solved within the scope of the first numerical optimization:

$$x_{local}^2 = \sum_{x \in u} D(x)^T D(x) - \Psi_E^T E \Psi_E - \Psi_O^T O \Psi_O - 2|\Psi_E^T O \Psi_O|, \quad (12)$$

This equation has no explicit dependency on the second phase $\phi_{EC}(x)$. This Equation (12) also has no explicit dependency on the weightings W, F of the water component 35 and the fat component 36.

The first phase $\Omega(x)$ can be determined by implementing the numerical optimization based on Equation (12). For example, the first numerical optimization can provide multiple result candidates for an image point 30. Particularly in such a case, the implementation of the first numerical optimization can furthermore include the implementation of a region growing technique. This is depicted in FIG. 6.

Figure 6:
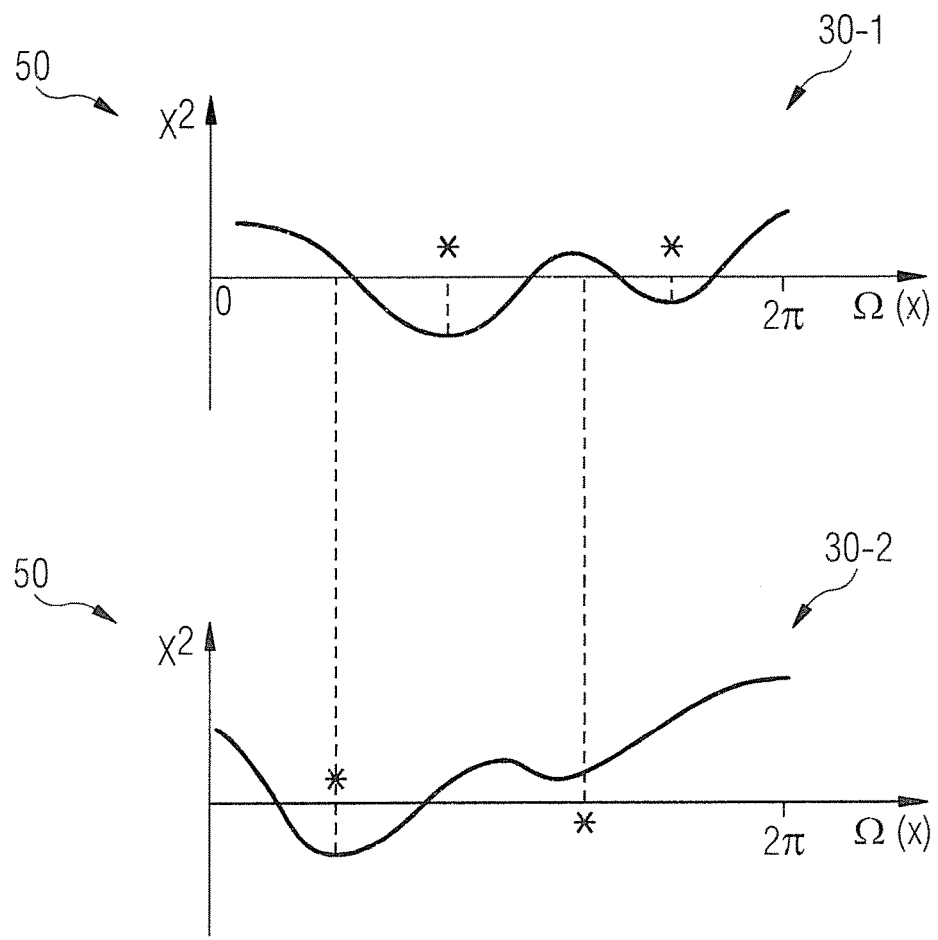
FIG. 6 illustrates numerical optimization for two image points.

In FIG. 6, a situation is shown in which the implementation of the first numerical optimization respectively provides two result candidates (labeled with stars in FIG. 6) for the image points 30-1, 30-2. In the scenario of FIG. 6, these image points 30-1, 30-2 are directly adjacent. The first numerical optimization can furthermore include the implementation of a region growing technique for the multiple image points 30-1, 30-2 of the MR data 25. For each image point 30-1, 30-2, a value can therefore be selected from the multiple result candidates as the first phase $\Omega(x)$. For example, after the smaller value of the first phase $\Omega(x)$ has been identified as the actual value for the physically relevant solution for the image point 30-2, the smaller value of the first phase $\Omega(x)$ could also be identified as the actual physically relevant solution for the image point 30-1 (respectively illustrated by an arrow and the vertical dashed lines in FIG. 6). In principle, region growing techniques are known to those skilled in the art in connection with the discovery of the relevant solution from multiple result candidates in connection with the optimization in Dixon techniques, such that no additional details need not be explained herein.

In the preceding, techniques have predominantly been described in relation to the implementation of the first numerical optimization. It is directly possible to also apply corresponding techniques in relation to the determination of the second phase $\phi_{EC}(x)$.

For example, based on Equation (5) a simultaneous numerical optimization could be implemented both with regard to the first phase $\Omega(x)$ and with regard to the second phase $\phi_{EC}(x)$. It would also be possible to computationally eliminate the first phase $\Omega(x)$ based on Equation (5), and therefore to obtain an equation (analogous to Equation (12)) that has no explicit dependency on the first phase $\Omega(x)$. This equation could then be solved within the scope of the numerical optimization to determine the second phase $\phi_{EC}(x)$.

However, a particularly simple and precise determination of the water content 35 and the fat content 36 can take place within the scope of the two-stage approach described in the preceding, in which initially the first phase $\Omega(x)$ is determined in the first numerical optimization and subsequently the second phase $\phi_{EC}(x)$ is determined within the scope of the second numerical optimization. In such a case, the equation on which the second numerical optimization is based can in particular have neither an implicit nor an explicit dependency on the first phase $\Omega(x)$. This is the case because the influence of the field inhomogeneities that are described by the first phase can be computationally eliminated from the MR data before the implementation of the second numerical optimization; a cleaning of the MR data is thus possible.

The equation on which the second numerical optimization is based can also have no implicit dependency on the water component 35 and the fat component 36. In particular, the weightings W, F of the water component 35 and the fat component 36 can be assumed to have real values.

The equation on which the second numerical optimization is based can then be described by a variable projection of the real-valued weightings W, F of both spectral portions 35, 36. This is presented in the following. Starting from Equation (4), the following equation can similarly be taken into account under the assumption that v(x) is real-valued.

$$x^2 = \|Av - \phi^T D\|^2, \qquad (13)$$

This Equation (13) is bilinear in the water component and fat component. Therefore, the water component and the fat component can be eliminated. This is designated as the variable projection. For this purpose, the matrix $A = A_R + iA_I$ can be split into the real part and imaginary part, wherein $A_R = \Re(A)$ and $A_I = \Im(A)$. This yields $$v(x) = (A_R^T A_R + A_I^T A_I)^{-1} \Re(A^T \phi(x)^T D(x)) \qquad (14)$$

$$= (A_R^T A_R + A_I^T A_I)^{-1} (A_R^T A_I^T) \begin{pmatrix} \Re(\phi(x)^T D(x)) \\ \Im(\phi(x)^T D(x)) \end{pmatrix}$$

From this is obtained:

$$x_{local}^2 = \sum_{x \in u} \left( D(x)^T D(x) - (\Re(\phi(x)^T D(x)) \Im(\phi(x)^T D(x))) \right. \qquad (15)$$

$$\left. \underbrace{\begin{pmatrix} A_R \\ A_I \end{pmatrix} (A_R^T A_R + A_I^T A_I)^{-1} (A_R^T A_I^T)}_{\equiv B_R} \begin{pmatrix} \Re(\phi(x)_T D(x)) \\ \Im(\phi(x)_T D(x)) \end{pmatrix} \right)$$

The matrix $B_R$ is real-valued, symmetrical, and has an order of 2 with eigenvalues 1, i.e. represents a projection onto the space that is spanned by the columns $(A_R, A_I)^T$. Therefore, it can be written: $B_R = \Sigma j_{=1,2} \tilde{w}_j \tilde{w}_j^T$, wherein the vectors $\tilde{w}_j = (w_{Rj}, w_{Ij})^T$ have real values and are orthogonal to one another. With the definition of $u_j = w_{Rj} + w_{Ij}$, $$x_{local}^2 = \sum_{x \in u} \left( D(x)^T D(x) - \sum_{j=1,2} |\Re(u_j^T \phi(x)^T D(x))|^2 \right) \qquad (16)$$

is obtained.

Using a comparison of Equations (7) and (16), the difference can be indicated between an approach in which the weightings W, F of the water component 35 and the fat component 36 are assumed as real-valued or, respectively, complex-valued. In Equation (7), it is not necessary to determine the real part (see Equation (16)), and the eigenvectors $u_j$ can be different depending on the imaginary part $A_I$.

Typically either the first phase $\Omega(x)$ or the second phase $\phi_{EC}(x)$ can be eliminated in the approach described above, which is based on the assumption of real-valued weightings such as W, F of the water component 25 and the fat component 36. Moreover, the phase $\phi$ at the first echo time is to be considered in order to also take into account relative phase shifts between the water portion 35 and the fat portion 36 after the excitation.

The preceding techniques form the basis of the subsequently described realizations: the determination of the first phase $\Omega(x)$ is typically predominantly independent of influences of the exposures, in particular if an approach according to Equation (12) is selected. On the other hand, the second phase $\phi_{EC}(x)$—which is obtained by the approach according to Equation (12)—often cannot be loaded (or can be loaded only to a limited extent), i.e. has large uncertainties. Therefore, within the scope of the implementation of the first optimization it can be worthwhile to take into account complex-valued weightings W, F for the water component 35 and the fat component 36 together with an equation that has no explicit dependency on the second phase $\phi_{EC}(x)$ while, within the scope of the implementation of the second optimization, an equation is considered that assumes real values of weightings W, F of the water component 35 and the fat component 36 and that has no implicit and no explicit dependency on the first phase $\Omega(x)$.

The realization described above—that the determination of the first phase $\Omega(x)$ has no or only a slight dependency on the second phase $\phi_{EC}(x)$—can be motivated based on the fact that the phases of the water component 35 and of the fat component 36 are not aligned for a scenario in which the water component 35 and the fat component 36 have a comparable order of magnitude—this can have strong influences on the determination of the second phase $\phi_{EC}(x)$ due to eddy current effects in an approach with complex-valued weightings W, F of the water component 35 and the fat component 36 according to Equation (7).

Based on this realization, Equation (16) can be reformulated to the effect that the first phase $\Omega(x)$ is assumed as given—namely according to the preceding determination—and only an optimization with regard to the second phase $\phi_{EC}(x)$ is implemented. In this case, $$x_{local}^2 = \sum_{x \in u} \left( D(x)^T D(x) - \sum_{j=1,2} \left| \Re \left( u_j^T e^{-i\phi} \phi_{EC}^T \underbrace{\phi_\Omega^T D(x)}_{=\tilde{D}(x)} \right) \right|^2 \right) \quad (17)$$

$$= \sum_{x \in u} D(x)^T D(x) - \frac{1}{4}$$

$$\sum_{j=1,2; x \in u} \left| ((u_j^T \phi_{EC}^T \tilde{D}(x))) e^{-i\phi} + (u_j^T \phi_{EC}^T D(x)) * e^{i\phi} \right|^2$$

$$= \sum_{x \in u} D(x)^T D(x) - \frac{1}{2}$$

$$\sum_{j=1,2; x \in u} \left| u_j^T \phi_{EC}^T \tilde{D}(x) \right|^2 - \frac{1}{2}$$

$$\sum_{j=1,2; x \in u} \Re \left( (u_j^T \phi_{EC}^T \tilde{D}(x))^2 e^{-2i\phi} \right)$$

is obtained.

After optimization in the phase $\phi$ at the echo time 21, $$x_{local}^2 = \quad (18)$$

$$\sum_{x \in u} D(x)^T D(x) - \frac{1}{2} \sum_{j=1,2; x \in u} \left| u_j^T \phi_{EC}^T \tilde{D}(x) \right|^2 - \frac{1}{2} \left| \sum_{j=1,2; x \in u} (u_j^T \phi_{EC}^T \tilde{D}(x))^2 \right|,$$

is obtained. This equation has no explicit dependency on the phase $\phi$ of the first echo time 21 and on the weightings W, F of the water component 35 and fat component 36. Equation (18) can serve as a basis of the second numerical optimization. The second numerical optimization can in turn provide multiple result candidates for an image point 30 of the MR data 25. The implementation of the second optimization can furthermore include the implementation of a region growing technique for the multiple image points 30 of the MR data, with a value from the multiple result candidates for each image point 30 being selected as a result.

The implementation of the first and second numerical optimization to determine the first phase and the second phase has been described in the preceding. The first phase $\Omega(x)$ and the second phase $\phi_{EC}(x)$ can therefore be determined. After the first phase and the second phase $\phi_{EC}(x)$ are determined, a field map of the field inhomogeneities and/or a field map of the eddy current effects can thus be provided to a user. The MR data 25 can be cleaned of the influence of the first phase $\Omega(x)$ before the implementation of the second numerical optimization to determine the second phase $\phi_{EC}(x)$. Alternatively, it is also possible for the previously determined first phase $\Omega(x)$ to be treated as an input parameter in the implementation of the second numerical optimization. It is also possible (as noted above) to initially implement the second numerical optimization to determine the second phase $\phi_{EC}(x)$, for example by the equation taken into account in having no explicit dependency on the first phase $\Omega(x)$, for example as is the case in Equation (17). The influence of the second phase $\phi_{EC}(x)$ on the MR data 25 can accordingly subsequently be purged, or the second phase $\phi_{EC}(x)$ could be treated as an input parameter in the implementation of the first numerical optimization to determine the first phase $\Omega(x)$.

In general, it is possible to assume the relaxation rate $R^*_{2,water}$ of the water component 35 and the relaxation rate $R^*_{2,fat}$ of the fat component 36 are zero within the scope of the first numerical optimization and/or within the scope of the second numerical optimization. The first and second numerical optimizations thus can be implemented without additional consideration of the relaxation rates, which simplifies the determination.

After the first phase $\Omega(x)$ and the second phase $\phi_{EC}(x)$ have been determined, their influences on the MR data 25 can be compensated and it can subsequently be assumed that: $\Omega(x)=1$ and $\phi(x)=1$. The relaxation constants of the water component 35 and of the fat component 36 can subsequently be calculated, based on:

$$x_{local}^2 = \sum_{x \in u} D(x)^T D(x) - \sum_{x \in u} D(x)^T PP^T D(x), \quad (19)$$

where only $PP^T$ is dependent on the relaxation constants. It is then possible to consider Equation (19) within the scope of the implementation of a numerical optimization which determines the relaxation rates of the water component (35) and fat component (36). An analytical calculation of the water component 35 and of the fat component 36 can subsequent take place under consideration of the previously determined relaxation rates.

In the preceding case described with regard to Equation (19), the equation on which the numerical optimization to determine the relaxation rates is based has no dependency on the first phase $\Omega(x)$ and/or on the second phase $\phi_{EC}(x)$. The dependency on the first phase $\Omega(x)$ and on the second phase $\phi_{EC}(x)$ was eliminated by the preceding numerical determination of the first phase $\Omega(x)$ and the second phase $\phi_{EC}(x)$ and purging of the influence of the first phase $\Omega(x)$ and the second phase $\phi_{EC}(x)$ on the MR data 25.

In the scenario described in the preceding, in which the numerical optimization to determine the relaxation rates is based on Equation (19), this also has no explicit dependencies on the water component 35 and the fat component 36. The explicit dependencies on the water component 35 and the fat component 36 were eliminated by a variable projection of the weightings W, F of the water component 35 and the fat component 36.

In addition to an evaluation of Equation (19) described in the preceding to determine the relaxation rates, a derivative can also be of interest:

$$\frac{d}{dR} x_{local}^2 = -\Re \left( \sum_{x \in u} D(x)^T \left( \frac{d}{dR} P \right) P^T D(x) \right), \quad (20)$$

wherein R is a real-value variable. For the case of Equation (20), a relatively simple selection of P and its derivative dP/dR is shown. In Equation (20a), an orthonormal basis of image space of A is obtained by Gram-Schmidt orthonormalization and the corresponding derivatives $$p_1 = a_1/|a_1| \quad (21)$$

$$b_2 = a_2 - (p_1^T a_2) p_1$$

$$p_2 = b_2/|b_2|$$

$$a_1' = \frac{d}{dR} a_1$$

$$|a_1'| = \Re(p_1^T a_1')$$

$$p_1' = a_1'/|a_1| - p_1 \Re(p_1^T a_1')/|a_1|$$

$$a_2' = \frac{d}{dR} a_2$$

$$b_2' = a_2' - (p_1^{T\prime} a_2) p_1 - (p_1^T a_2') p_1 - (p_1^T a_2) p_1'$$

$$|b_2'| = \Re(p_2^T b_2')$$

$$p_2' = b_2'/|b_2| - p_2 \Re(p_2^T b_2')/|b_2|,$$

In this way, the base and its derivative can be calculated on a grid, and the best local minimum can be determined depending on these. The physical relevant solution can therefore be selected from a number of result candidates that supplies the numerical optimization to determine the relaxation rates of the water component 35 and fat component 36.

For example, the water component 35 and fat component 36 can also be calculated analytically based on Equation (21), or by a variable back-projection.

For example, given known values of the relaxation rates the water component 35 and fat component 36 for complex-valued weightings W, F can be calculated via $$v(x) = (A(A^T A)^{-1} A^T D(x)) \quad (22)$$

For real-value weightings W, F of the water component 35 and fat component 36, $$v(x) = (\Re(A^T A)))^{-1} \Re(A^T D(x)) \quad (23)$$

is obtained. The fat component then results as:

$$\left|\frac{F}{W+F}\right|. \quad (24)$$

Since only the magnitude of the complete expression is taken instead of determining the magnitudes separately for the weightings W and F, a particularly good signal-to-noise ratio can be obtained.

Figure 7:
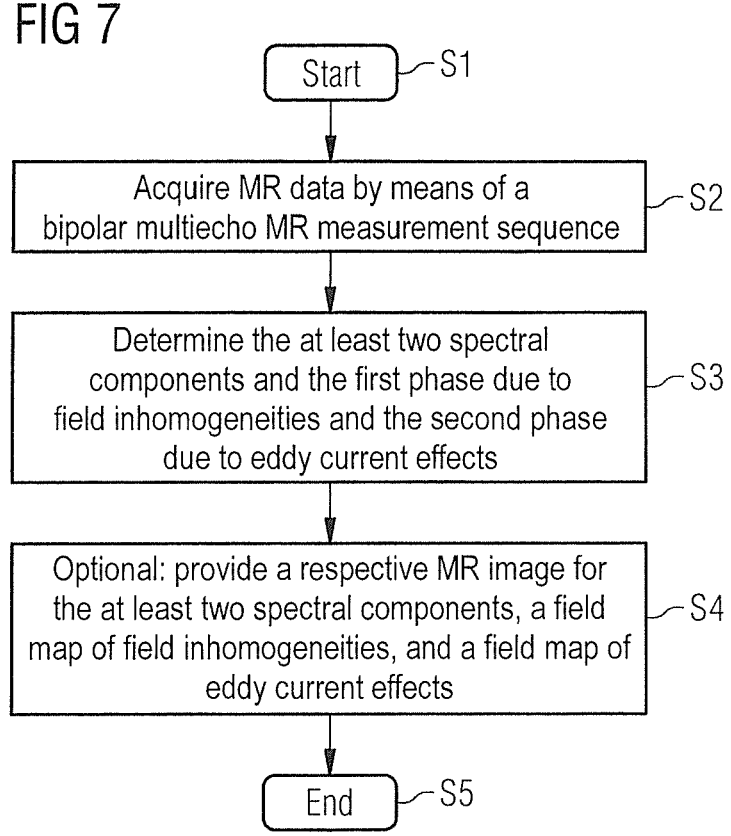
FIG. 7 is a flowchart of an embodiment of the method according to various embodiments.

A flowchart of a method according to various aspects of the present invention is shown in FIG. 7. The method begins in step S1. In step S2, the MR data 25 are acquired by means of the bipolar multi-echo MR measurement sequence 5 (see FIG. 2). In particular, a bipolar gradient echo MR measurement sequence can be applied in which the readout gradient fields 16-1, 16-2, 16-3 are alternately applied in opposite directions. MR signals at at least three echo times 21, 22, 23 can thereby be acquired for each image point 30. For example, the echo times 21, 22, 23 can be equidistantly spaced.

The determination of the at least two spectral components and the first phase $\Omega(x)$ and the second phase $\phi_{EC}(x)$ subsequently takes place in Step S3. The determination in Step S3 takes place numerically at least in part, for example in that one or more numerical optimizations are implemented. However, the determination within the scope of step S2 can also have analytical calculation steps.

For example, in a particularly simple embodiment the Equation (4) or Equation (5) described in the preceding can take place within the scope of a single numerical optimization to determine the water component 35, the fat component 36, the first phase $\Omega(x)$ and the second phase $\phi_{EC}(x)$. Within the scope of step S3 it is also possible to implement multiple steps in which individual instances of these variables cited in the preceding are respectively determined separately.

The provision of a respective MR image for the at least two spectral components 35, 36 subsequently takes place in step S4 (optional step). Alternatively or additionally, a field map of the field inhomogeneities is shown based on the determined first phase $\Omega(x)$. Alternatively or additionally, it is possible that a field map of the eddy current effects is provided based on the determined second phase $\phi_{EC}(x)$. The method ends in step S5.

Figure 8:
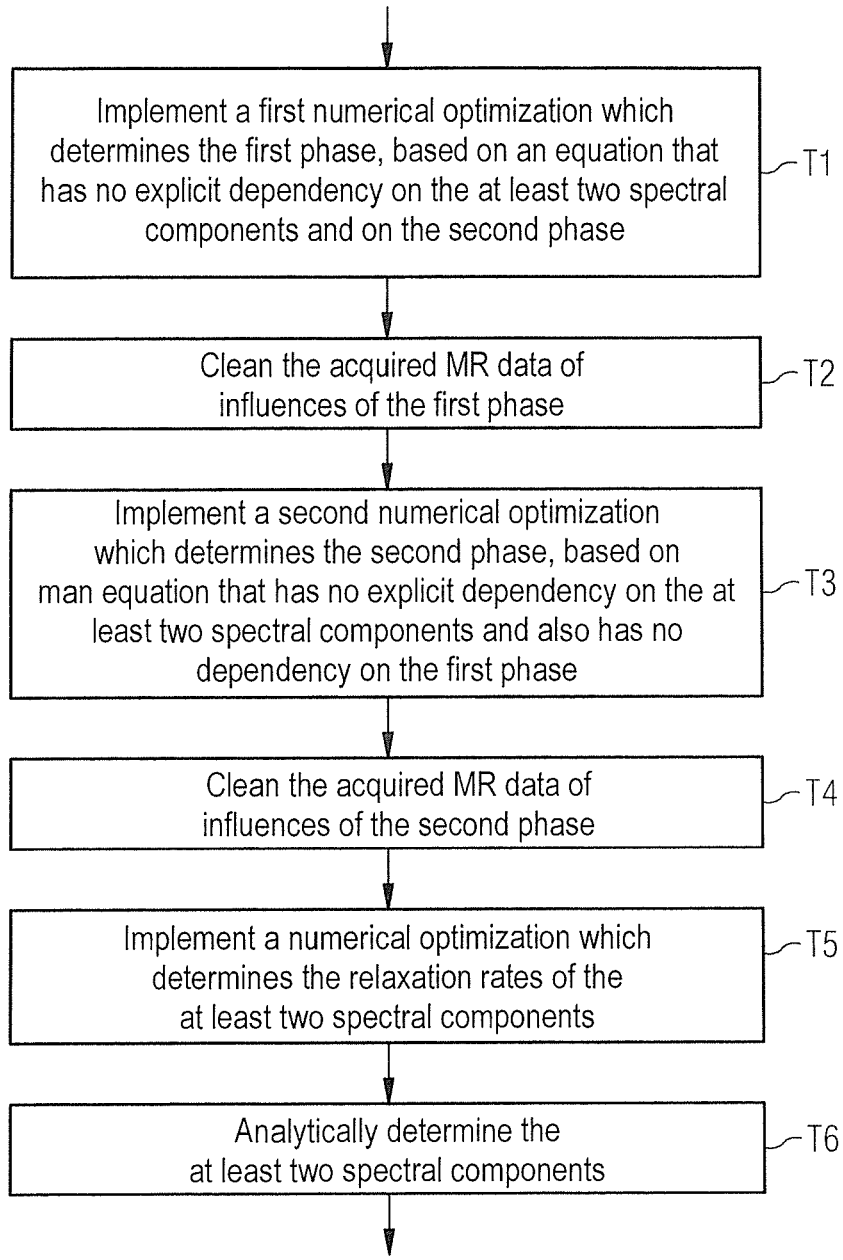
FIG. 8 is a flowchart that illustrates details of the flowchart of FIG. 7.

In FIG. 8, a flow diagram is shown which presents details regarding the step S3 described in the preceding. The implementation of the steps T1-T6 rendered in FIG. 8 can thus take place within the scope of Step S3.

The implementation of the first numerical optimization which determines the first phase $\Omega(x)$ based on field inhomogeneities initially takes place in Step T1. Step T1 is based on an equation that has no explicit dependency on the at least two spectral components 35, 36 and also has no explicit dependency on the second phase $\Omega(x)$, $\phi_{EC}(x)$. The numerical optimization can thus be implemented in step T1, for example on the basis of Equation (12).

The cleaning of the MR data 25 of influences of the first phase $\Omega(x)$ can subsequently take place in Step T2 (optional step). After the implementation of Step T2, the acquired MR data have no or only a small implicit and explicit dependency on the first phase $\Omega(x)$. This means that influences of the field inhomogeneities of the basic magnetic field on the MR data 25 are suppressed.

The implementation of the second numerical optimization which determines the second phase $\phi_{EC}(x)$ subsequently takes place in Step T3. The implementation of the second numerical optimization is based on an equation that has no explicit dependency on the at least two spectral components 35, 36 and also has no dependency on the first phase $\Omega(x)$. For example, Step T3 can be based on Equation (18).

The equation on which the implementation of the second numerical optimization in Step T3 is based can take place by a variable projection with regard to the real-value, assumed weightings W, F of the water component 35 and of the fat component 36. In one case in which the weightings W, F are assumed to have real values, the phase $\phi$ at the first echo time 21 can additionally be taken into account. The equation on which the numerical optimization in Step T3 is based may have no explicit dependency on the phase $\phi$ at the first echo time 21. For example, this can be achieved by computational elimination of the phase $\phi$ at the first echo time from the equation that is obtained using the variable projection based on the spectral model (see Equations (17) and (18)).

The purging of the acquired MR data 25 of influences of the second phase $\phi_{EC}(x)$ subsequently takes place in Step T4. Steps T4 and T2 can have corresponding techniques.

The implementation of the numerical optimization to determine the relaxation rates of the at least two spectral components 35, 36 takes place in Step T5. The equation on which the numerical optimization of Step T5 is based can in turn have no explicit dependency on the at least two spectral components 35, 36. For example, the explicit dependency can in turn be eliminated by variable projection based on the spectral model, for example under the assumption of real-value weightings W, F of the water component 35 and of the fat component 36. For example, Step T5 can be implemented with Equation (19).

The analytical determination of the at least two spectral components takes place in Step T6.

The features of the embodiments and aspects of the invention described in the preceding can naturally be combined with one another. In particular, the features can be used not only in the described combinations but also in other combinations or independently, without departing from the scope of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring magnetic resonance data from an examination subject, comprising:
   operating a magnetic resonance data acquisition unit, that generates a basic magnetic field in which an examination subject is situated, according to a bipolar multi-echo data acquisition sequence, to acquire magnetic resonance data from the examination subject for multiple image points by, for each image point, alternatingly activating positive and negative readout gradient fields with a gradient system of said acquisition unit, during which magnetic resonance signals are read out during at least three echo times, said activation of said gradient fields producing eddy currents in said data acquisition unit by interaction with said basic magnetic field;
   providing said magnetic resonance data to a computerized processor and, in said computerized processor, operating on said magnetic resonance data with a spectral model of a multipoint Dixon technique that relates said magnetic resonance data to at least two spectral components of said magnetic resonance signals and respective, associated relaxation rates of said at least two spectral components, and a first phase of said magnetic resonance signals that occurs due to field inhomogeneities of said basic magnetic field, and a second phase that occurs due to effects of said eddy currents, to implement an at least partially numerical determination of said at least two spectral components, said relaxation rates, said first phase, and said second phase; and
   making said at least two spectral components available in electronic form at an output of said processor in a format allowing reconstruction of an in-phase image and two out-of-phase images according to the multipoint Dixon technique that is modeled by said spectral model.

2. A method as claimed in claim 1 wherein said spectral model comprises a positive prefactor of said second phase for said magnetic resonance signals that are read out when said positive gradient fields are activated, and a negative prefactor of said second phase for said magnetic resonance signals that are read out when said negative readout gradient fields are activated.

3. A method as claimed in claim 1 comprising:
   in said computerized processor, determining a computational grid of lower resolution relative to a resolution of said magnetic resonance data, wherein each grid point of said computational grid includes a predetermined number of adjacent image points of said magnetic resonance data; and
   in said partially numerical determination of said first phase and said second phase, using an equation that is based on at least one of said first phase and said second phase being constant within a grid point of said computational grid.

4. A method as claimed in claim 1 comprising, in said at least partially numerical determination:
   implementing a first numerical optimization that determines said first phase;
   purging said magnetic resonance data of influences of said first phase depending on the determined first phase;
   implementing a second numerical optimization that determines said second phase; and
   purging the magnetic resonance data of influences of said second phase dependent on the determined second phase.

5. A method as claimed in claim 4 comprising:
   implementing said first numerical optimization to produce multiple result candidates for an image point;
   in said first optimization, implementing a region growing technique for said multiple image points in order to select a value for the multiple result candidates for each of said image points.

6. A method as claimed in claim 5 comprising implementing first numerical optimization, using an equation having no explicit dependency on at least one of said at least two spectral components.

7. A method as claimed in claim 4 comprising:
   implementing said second numerical optimization to produce multiple result candidates for an image point;
   in said second optimization, implementing of a region growing technique for said multiple image points in order to select a value for the multiple result candidates for each of said image points.

8. A method as claimed in claim 7 comprising implementing said second numerical optimization using an equation having no explicit dependency on at least one of said at least two spectral components.

9. A method as claimed in claim 4 comprising:
   implementing said first numerical optimization to produce multiple result candidates for an image point;
   in said first optimization, implementing of a region growing technique for said multiple image points in order to select a value for the multiple result candidates for each of said image points;
   implementing said second numerical optimization to produce multiple result candidates for an image point; and
   in said second optimization, implementing a region growing technique for said multiple image points in order to select a value for the multiple result candidates for each of said image points.

10. A method as claimed in claim 9 comprising implementing said first numerical optimization using an equation having no explicit dependency on at least one of said at least two spectral components, and implementing said second numerical optimization using an equation having no explicit dependency on at least one of said at least two spectral components.

11. A method as claimed in claim 10 wherein said equation used in implementing said first numerical optimization comprises a variable projection of complex-valued weightings of said at least two spectral components, and wherein said equation used in implementing said second numerical optimization comprises a variable projection of real-value weightings of said at least two spectral components.

12. A method as claimed in claim 11 wherein said equation used in implementing said second numerical optimization additionally comprises a phase at a first of said at least three echo times.

13. A method as claimed in claim 4 comprising:
implementing said first numerical optimization using an equation having no explicit dependency on said second phase; and
implementing said second numerical optimization using an equation that has no explicit dependency on said first phase.

14. A method as claimed in claim 4 comprising implementing said first numerical optimization using an equation that assumes a relaxation rate for said at least two spectral components that is equal to zero.

15. A method as claimed in claim 1 comprising determining said at least two spectral components with respective associated relaxation rates by:
implementing a numerical optimization that determines said relaxation rates of said at least two spectral components; and
implementing an analytical calculation of said at least two spectral components dependent on the determined relaxation rates.

16. A method as claimed in claim 15 comprising implementing said numerical optimization to determine said relaxation rate with no dependency on said first phase.

17. A method as claimed in claim 16 comprising giving said numerical optimization that determines said relaxation rates no dependency on said first phase by purging said magnetic resonance data of dependency on said first phase using a preceding numerical determination of said first phase.

18. A method as claimed in claim 15 comprising implementing said numerical optimization to determine said relaxation rates with no dependency on said second phase.

19. A method as claimed in claim 18 comprising giving said numerical optimization that determines said relaxation rates no dependency on said second phase by purging said magnetic resonance data of dependency on said second phase using a preceding numerical determination of said second phase.

20. A method as claimed in claim 15 comprising;
implementing said numerical optimization to determine said relaxation rates with no dependency on said first phase; and
implementing said numerical optimization to determine said relaxation rates with no dependency on said second phase.

21. A method as claimed in claim 20 comprising:
giving said numerical optimization that determines said relaxation rates no dependency on said first phase by purging said magnetic resonance data of dependency on said first phase using a preceding numerical determination of said first phase; and
giving said numerical optimization that determines said relaxation rates no dependency on said second phase by purging said magnetic resonance data of dependency on said second phase using a preceding numerical determination of said second phase.

22. A method as claimed in claim 15 comprising implementing said numerical optimization to determine said relaxation rates with no explicit dependency on said at least two spectral components using an equation comprising a variable projection of weightings of said at least two spectral components.

23. A magnetic resonance apparatus comprising:
a magnetic resonance data acquisition unit comprising a basic field magnet that generates a basic magnetic field in which an examination subject is situated, and a gradient system;
a control computer configured to operate the magnetic resonance data acquisition unit, according to a bipolar multi-echo data acquisition sequence, to acquire magnetic resonance data from the examination subject for multiple image points by, for each image point, alternatingly activating positive and negative readout gradient fields with said gradient system, during which magnetic resonance signals are read out at at least three echo times, said activation of said gradient fields producing eddy currents in said data acquisition unit by interaction with said basic magnetic field;
a computerized processor provided with said magnetic resonance data said computerized processor, being configured to operate on said magnetic resonance data with a spectral model of a multipoint Dixon technique that relates said magnetic resonance data to at least two spectral components of said magnetic resonance signals and respective, associated relaxation rates of said at least two spectral components, and a first phase of said magnetic resonance signals that occurs due to field inhomogeneities of said basic magnetic field, and a second phase that occurs due to effects of said eddy currents, to implement an at least partially numerical determination of said at least two spectral components, said relaxation rates, said first phase, and said second phase; and
said computerized processor being configured to make said at least two spectral components available in electronic form at an output of said processor in a format allowing reconstruction of an in-phase image and two out-of-phase images according to the multipoint Dixon technique that is modeled by said spectral model.

24. A method for acquiring magnetic resonance data from an examination subject, comprising:
operating a magnetic resonance data acquisition unit, that generates a basic magnetic field in which an examination subject is situated, according to a bipolar multi-echo data acquisition sequence, to acquire magnetic resonance data from the examination subject for multiple image points by, for each image point, alternatingly activating positive and negative readout gradient fields with a gradient system of said acquisition unit, during which magnetic resonance signals are read out during at least three echo times;
providing said magnetic resonance data to a computerized processor and, in said computerized processor, operating on said magnetic resonance data with a spectral model of a multipoint Dixon technique that relates said magnetic resonance data to at least two spectral components of said magnetic resonance signals and respective, associated relaxation rates of said at least two spectral components, and a first phase of said magnetic resonance signals that occurs due to field inhomogeneities of said basic magnetic field, and a different second phase that occurs due to effects of a source of disturbance to said magnetic resonance data other than said field inhomogeneities, to implement an at least partially numerical determination of said at least two spectral components, said relaxation rates, said first phase, and said second phase; and making said at least two spectral components available in electronic form at an output of said processor in a format allowing reconstruction of an in-phase image and two out-of-phase images according to the multipoint Dixon technique that is modeled by said spectral model.

25. A magnetic resonance apparatus comprising:

a magnetic resonance data acquisition unit comprising a basic field magnet that generates a basic magnetic field in which an examination subject is situated, and a gradient system;

a control computer configured to operate the magnetic resonance data acquisition unit, according to a bipolar multi-echo data acquisition sequence, to acquire magnetic resonance data from the examination subject for multiple image points by, for each image point, alternatingly activating positive and negative readout gradient fields with said gradient system, during which magnetic resonance signals are read out at at least three echo times;

a computerized processor provided with said magnetic resonance data said computerized processor, being configured to operate on said magnetic resonance data with a spectral model of a multipoint Dixon technique that relates said magnetic resonance data to at least two spectral components of said magnetic resonance signals and respective, associated relaxation rates of said at least two spectral components, and a first phase of said magnetic resonance signals that occurs due to field inhomogeneities of said basic magnetic field, and a different second phase that occurs due to effects of a source of disturbance to said magnetic resonance data other than said field inhomogeneities, to implement an at least partially numerical determination of said at least two spectral components, said relaxation rates, said first phase, and said second phase; and said computerized processor being configured to make said at least two spectral components available in electronic form at an output of said processor in a format allowing reconstruction of an in-phase image and two out-of-phase images according to the multipoint Dixon technique that is modeled by said spectral model.

* * * * *